(12) United States Patent
Kulcsar

(10) Patent No.: US 8,178,080 B2
(45) Date of Patent: May 15, 2012

(54) HAIR CARE COMPOSITIONS

(75) Inventor: Lidia Kulcsar, Bronx, NY (US)

(73) Assignee: Avon Products, Inc., New York, NY (US)

( * ) Notice: Subject to any disclaimer, the term of this patent is extended or adjusted under 35 U.S.C. 154(b) by 530 days.

(21) Appl. No.: 12/112,447

(22) Filed: Apr. 30, 2008

(65) Prior Publication Data

US 2009/0274640 A1 Nov. 5, 2009

(51) Int. Cl.
*A61K 8/87* (2006.01)
*A61Q 5/12* (2006.01)

(52) U.S. Cl. .................................................. 424/70.12

(58) Field of Classification Search ........................ None
See application file for complete search history.

(56) References Cited

U.S. PATENT DOCUMENTS

| | | |
|---|---|---|
| 5,045,307 A | 9/1991 | Marschner et al. |
| 5,922,310 A | 7/1999 | Chaudhuri et al. |
| 6,129,909 A | 10/2000 | Bonda et al. |
| 6,143,286 A | 11/2000 | Bhambhani et al. |
| 6,180,091 B1 | 1/2001 | Bonda et al. |
| 7,169,396 B2 | 1/2007 | Hahn et al. |
| 2005/0188481 A1 | 9/2005 | Vona, Jr. |
| 2006/0008437 A1* | 1/2006 | Robinson et al. ............ 424/70.1 |
| 2007/0077217 A1 | 4/2007 | King et al. |
| 2007/0081954 A1 | 4/2007 | Mougin et al. |
| 2007/0202068 A1 | 8/2007 | Walter et al. |
| 2008/0038206 A1 | 2/2008 | Steinbrecht et al. |
| 2009/0151086 A1* | 6/2009 | Brun ................................ 8/405 |

* cited by examiner

*Primary Examiner* — David J Blanchard
*Assistant Examiner* — Garen Gotfredson
(74) *Attorney, Agent, or Firm* — Joan M. McGillycuddy; Charles J. Zeller; David M. Joyal

(57) ABSTRACT

Hair care compositions are disclosed which comprise a silicone polyurethane polymer, an ester, and a fluorosilicone. The compositions are useful for improving color retention of artificially colored hair.

16 Claims, No Drawings

HAIR CARE COMPOSITIONS

FIELD OF INVENTION

The present invention relates generally to compositions for the hair. More specifically, the invention relates to cosmetic compositions for improving color retention in artificially colored hair and/or for imparting films on the hair having enhanced shine and feel.

BACKGROUND OF THE INVENTION

Consumers have utilized a number of cosmetic and personal care compositions to enhance and/or modify the appearance of keratin fibers, such as the hair. One popular modification is impartation of an artificial color on the hair using a chemical dye. For example, the hair may be treated using a direct dye or an oxidative dye, which is also known as a "permanent" hair dye, to obtain a desired color.

It is known in the art that artificial hair colors, particularly red tones, obtained by treating hair with chemical dyes rapidly fade with repeat shampooing and washing. The chemical dyes used to impart color on the hair tend to increase the porosity of the keratin fibers of the hair. The increased porosity provides an increased surface area and allows an increased flow of fluids (e.g., water) through the fibers of the hair and thus, increases the rate at which molecules of the chemical dyes are leached from the hair. Artificially colored hair may exhibit substantial color fading after only a few washings. Specifically, it has been shown that more than 20% of the artificial hair color can be lost during the first five washes.

Most hair care products currently available (e.g., conditioner, hair gel, hairspray) are specifically formulated as hydrophilic compositions. Such hair products can be easily removed using water, with or without the addition of shampoo, exposing the fibers of the hair to direct contact with water and thereby permitting the chemical dye molecules to be leached from the hair. For example, U.S. Pat. No. 6,706,674 describes a hair styling composition comprising a vinyl copolymer and a nonaqueous solvent. The nonaqueous solvent may comprise a polyhydric $C_2$-$C_6$ alcohol. It is stated that certain embodiments of the hair styling composition may comprise triisostearyl trilinoleate as a viscosity controlling agent and/or a Fluoro $C_{2-8}$ alkyldimethicone as an emollient.

Recent advances to enhance color retention and/or reduce color fading of artificially colored hair have included the use of color-protecting agents. Typically, these color-protecting agents can be incorporated into hair care compositions through emulsification, dissolution or otherwise made to be compatible with such hair care product compositions. The color-protecting agents may include mild surfactants, cationic conditioning agents, aminofunctional silicones, ultraviolet absorbers, starches or sugar surfactants.

For example, U.S. Pat. No. 5,922,310 describes a composition for preventing the fading of artificial hair dye and/or slowing down the oxidation of hair comprising a cationic antioxidant phenol.

U.S. Pat. Nos. 6,129,909 and 6,180,091 describe a hair-treating composition comprising a diester or polyester of a naphthalene dicarboxylic acid for imparting gloss and/or hair color stabilization. It is stated that the naphthalene dicarboxylic acid can be mixed in an aqueous phase of the hair-treating composition to impart improved photo-stabilizing properties.

U.S. Pat. No. 5,045,307 describes a method of treating dyed hair to reduce the color loss caused by exposure to the ultraviolet rays of the sun by applying an effective amount of a hair treating formulation comprising an effective amount of a water insoluble benzophenone compound that combines readily with a hair substantive carrier composition.

U.S. Pat. No. 6,143,286 describes hair conditioning compositions comprising a cationic conditioning agent, a fatty alcohol, a nonionic surfactant and a particular siloxane polymer having both difunctional units and trifunctional units, in a ratio of about 10 to 80 difunctional units for every trifunctional unit.

U.S. Patent Publication 2005/0188481 describes a compositing comprising at least one amylose-containing starch, and its use in extending or improving the color durability and stability of artificially colored hair.

A number of hair dye manufacturers have incorporated color-protecting agents in "color sealing" conditioners to be used after the first shampooing of newly artificially colored hair. However, the use of such a conditioner cannot provide enhanced color retention and/or reduced color fading during the first shampooing. During the first shampooing, the newly artificially colored hair is not protected from water or shampoo. Therefore, a noticeable amount of the chemical dye molecules can be leached from the hair at that time, causing the newly artificially colored hair to suffer a substantial amount of color fading before a color-protecting agent is applied.

Despite the advances for color-protecting agents, there remains a need in the art for enhanced color retention and/or reduced color fading of artificially colored hair. It is therefore an object of the invention to provide compositions and methods for imparting enhanced color retention and reduced color fading to artificially colored hair.

SUMMARY OF THE INVENTION

In accordance with the foregoing objectives and others, the present invention provides hair care compositions that impart improved color retention or reduced color fading to artificially colored hair.

In one aspect of the invention hair care compositions for improving color retention in dyed hair are provided comprising at least two of, and preferably all three of (i) a silicone polyurethane polymer, (ii) a film-forming ester, and (iii) a fluorosilicone, in a suitable vehicle. In various implementations, the silicone polyurethane is Bis-Hydroxypropyl Dimethicone/SMDI copolymer, and/or the film-forming ester is Triisostearyl Trilinoleate, and/or the flurosilicone is Perfluorononyl Dimethicone. The vehicle is preferably one in which the silicone polyurethane polymer, film-forming ester, and fluorosilicone are dispersible but not soluble. An example of such a vehicle is an aqueous system comprising water and a thickener, such as a cationic thickener.

In yet another aspect of the invention, a method for improving color retention of artificially colored hair is provided comprising applying to dyed hair any of the inventive compositions. The compositions may be applied to wet hair or to dry hair, may be applied immediately after dyeing, prior to the first washing (shampooing) after dyeing, or even after the first, second, or third washing while still providing a measurable resistance against color fading.

These and other aspects of the present invention will become apparent to those skilled in the art after a reading of the following detailed description of the invention, including the illustrative embodiments and examples.

DETAILED DESCRIPTION

In the following description of the invention, it is to be understood that the terms used herein have their ordinary and accustomed meanings in the art, unless otherwise specified. All weights percentages referred to herein are given in terms of "% by weight" of the total composition, unless otherwise indicated.

The term "hair" refers to any hair of the body, including hair of the scalp, eyelashes, moustache, beard, and the like. In the preferred practice, the compositions are applied to the hair of the scalp.

The present invention is founded, in part, on the discovery that the film-forming ester Triisostearyl Trilinoleate provides robust, water and surfactant resistant films, particularly in combination with a silicone polyurethane polymer and/or fluorosilicone. The inventive combination provides effective color retention and reduced color fading of artificially colored hair, particularly after repeated shampooing. Further, this combination imparts a desirable feel to the hair.

The preferred composition generally comprises a combination of a silicone polyurethane polymer, a film-forming, hydrophobic ester, and a fluorosilicone which is preferably both hydrophobic and oleophobic. This novel combination has been found to improved color retention and/or reduced color fading of artificially colored hair.

Without wishing to be bound by any theory, it is believed that the inventive combination forms water-resistant films onto keratin fiber that serve as protective barriers against water and/or shampoo and improve retention of dye molecules in artificially colored hair. The water-resistant films cannot be easily removed with water alone or with shampoo, and thus retard the rate at which molecules of chemical dyes are leached from the hair.

The inventive compositions are contemplated to impart improved color retention and/or reduced color fading of artificially colored hair over any range of relative proportions of silicone polyurethane polymer (a) to ester (b) to fluorosilicone (c), the ratio of which is represented by a:b:c, Typically, a, b and c independently range from about 1 to about 50, more typically from about 1 to about 25, and usually from about 1 to about 10. Preferably, a, b, and c independently range from about 1 to about 5, more preferably from about 1 to about 3, and more preferred still from about 1 to about 2, including a weight ratio of silicone polyurethane polymer to ester to fluorosilicone from about 1:1:1 to about 10:1:10, more typically from about 1:1:1 to about 5:1:5, and usually of about 1:1:1.

It is believed that the combination of the three principal components achieves benefits not seen with each component individually or with an otherwise identical compositions lacking the silicone polyurethane polymer, the ester, or the fluorosilicone.

A first component according to some embodiments of the inventive compositions is a silicone polyurethane polymer. There is essentially no restriction on the nature of the silicone polyurethane polymer and any polymer comprising organosiloxane units and urethane linkages is contemplated to be useful in the practice of the invention.

In one embodiment, the silicone polyurethane polymer will be the reaction product of a hydroxyl functionalized polyorganosiloxane, preferably containing two or more hydroxyl groups, with a diisocyantate moiety. The hydroxyl functionalized polyorganosiloxane will typically have the structure of Formula I:

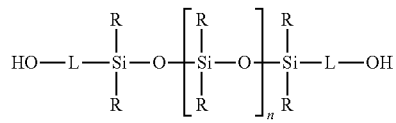

where R is selected independently at each occurrence from hydrogen, hydroxyl, and optionally substituted hydrocarbon groups containing from 1 to 10 carbon atoms, and in particular from optionally substituted alkyl, alkenyl, alkynyl, aryl, alkyl-aryl, or aryl-alkyl groups; preferably R is selected from optionally substituted branched, straight chain, or cyclic $C_{1-6}$ alkyl or alkenyl groups, including without limitation, methyl, ethyl, propyl, isopropyl, butyl, isobutyl, t-butyl, amyl, hexyl, cyclohexyl, vinyl, allyl, and the like or $C_{1-8}$ aryl, alkyl-aryl, or aryl-alkyl groups, including without limitation, phenyl, benzyl, tolyl, xylyl and the like;

wherein each of the foregoing R groups may include optional substitution by one or more heteroatoms, including oxygen, nitrogen, phosphorous, and halogen, particularly fluorine, as exemplified by fluoroalkyl (including perfluoroalkyl) groups, such as mono-, di-, and tri-fluoromethyl, perfluorophenyl, and the like, amino-substituted $C_{1-6}$ alkyl groups, including those having the form $—(CH_2)_{1-6}—NR^N_2$ and $—(CH_2)_{1-6}—NR^N—(CH_2)_{1-6}NR^N_2$ where $R^N$ is typically hydrogen, but may be methyl, ethyl, propyl, and the like, polyether groups including without limitation, polyethyleneoxide groups of the form $—(CH_2CH_2O)_n—$, polypropylene oxide groups of the form $—(CH(CH_3)CH_2O)_n—$ and combinations thereof; and amine oxide, phosphate, hydroxyl, ester, and/or carboxylate functionalities, and the like; or wherein R may comprise an additional group -L-OH;

wherein L either represents a bond or a linker group; preferably L is a linker group selected from divalent hydrocarbons having from 1 to 10 carbon atoms, including divalent alkyl, alkenyl, alkynyl, aryl, alkyl-aryl, or aryl-alkyl groups, as exemplified by $C_{1-10}$ alkyl groups, including without limitation, divalent groups of the form $—(CH_2)_{1-10}—$, preferably $—(CH_2)_{1-6}—$, and more preferably, L is $—CH_2CH_2CH_2—$;

and where n is an integer from 0 to 5,000, preferably from 1 to 200, more preferably from 1 to 100, and more preferred still from 10 to 50. Preferably R represents methyl at least one or more occurrences, more preferably, R represents methyl at all or substantially all occurrences, by which is meant that R represents methyl at greater than 90%, 95% or 98% occurrences.

In one embodiment according to the invention, the hydroxyl functionalized polyorganosiloxane pre-polymer comprises a polymethylsiloxane, and has the structure of Formula Ia:

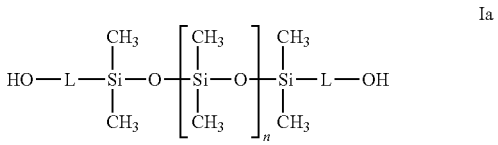

where L and n are as defined previously. In a preferred embodiment of the invention, the hydroxyl functionalized polyorganosiloxane is Bis-Hydroxypropyl Dimethicone, which comprises a polymethylsiloxane, and has the structure of Formula Ib:

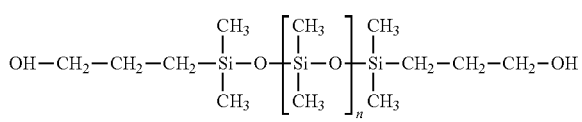

where n is as defined above.

The diisocyanate will be of the form $O=C=N-R^1-N=C=O$, where $R^1$ is a divalent hydrocarbon group containing from 1 to 20 carbon atoms, including optional substitution with one or more heteroatoms, and in particular $R^1$ will be selected from optionally substituted, branched, straight chain, or cyclic alkyl, alkenyl, alkynyl, aryl, alkyl-aryl, or aryl-alkyl groups; including without limitation:

(i) a group of the form:

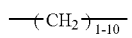

(ii) a group of the form:

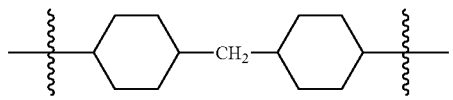

(iii) a group of the form:

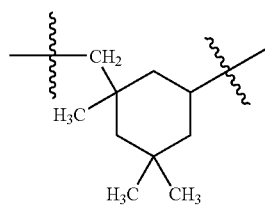

(iv) a group of the form:

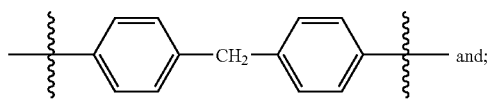

(v) a group of the form:

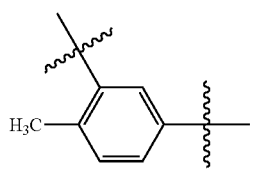

and combinations thereof

Suitable diisocyanates include, without limitation, dicyclohexylmethane-4,4'-diisocyanate (SMDI); toluene diisocyanate; methylene diphenyl diisocyanate, including 2,2'-MDI, 2,4'-MDI, and 4,4'-MDI; 1,6-hexamethylene diisocyanate, isophorone diisocyanate; methylene dicyclohexyl diisocyanate; xylene diisocyanate; cyclohexane diisocyanate; 3,3'-dimethyl-4,4'-diphenylmethane diisocyanate; p-phenylene diisocyanate; m-phenylene diisocyanate, 4,4'-isopropylidene dicyclohexyl isocyanate; and the like. In a preferred embodiment, the diisocyanate will comprise, consist essentially of, or consist of SMDI.

The polyorganosiloxane polyurethane polymer will comprise repeat units derived from the hydroxyl functionalized polyorganosiloxane and the diisocyanate in the form of an AB alternating copolymer, where unit A has the structure of Formula II:

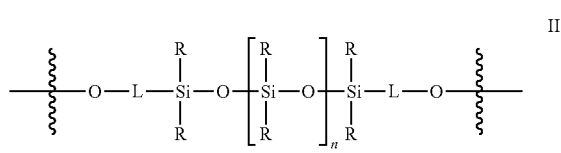

where R, L, and n are as defined previously in relation to Formula I, Ia, and Ib, and where unit B has the structure of Formula III:

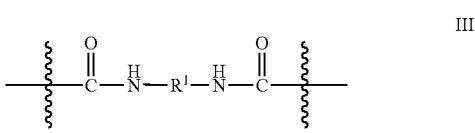

where $R^1$ is as defined previously, and wherein units A and B are arranged in a linear, branched, or cyclic configuration.

When the polymer is a cyclic polymer, it may be represented as:

where z is an integer value from 2 to 2,000. Where the polyorganosiloxane polyurethane polymer is cyclic, the propagation of the polymer is self-terminating. However, in the case of a linear polymer, termination may be accomplished by, for example, allowing the polymerization reaction to run to completion, employing a stoichiometric excess of dihydroxyl polyorganosiloxane of Formula I in relation to diisocyanate, quenching the reaction with a mono-alcohol or an amine, for example a dialkyl amine, including in the reaction mixture quantities of monofunctional reactants, such as mono-hydroxyl polyorganosiloxane analogs of Formula I, and/or mono-functional isocyanate reactants, or any other suitable method for terminating the urethane polymerization reaction. Thus, the polyorganosiloxane polymers may have a variety of terminating groups, including without limitation, hydroxyl groups, including the group -L-OH, tri-alkylsilyl groups, including trimethylsilyl, hydrocarbons, such as linear, branched or cyclic alkyl or aryl groups which may, amines, cabinol, silanols and the like.

The polymer may also include branching or grafting points in the polyorganosiloxane where one or more groups R in Formula I or II is a group such as:

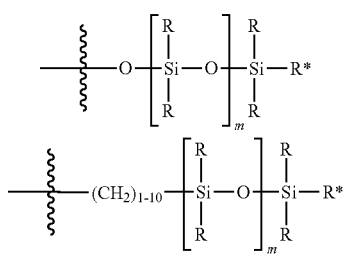

where R is as defined for Formula I, and R* may represent a group -L-O— further coupling the side chain to a unit B of Formula III, which may in turn be further coupled to unit A of Formula II, and so on, or R* may represent -L-OH, a group R, as defined previously, or a terminating group. When the polyorganosiloxane comprises branch or graft points of this type, they may be present as T-type or Q-type branches or grafts, where T denotes that only one R group on a Si atom is a polyorganosiloxane chain as shown above and Q denotes that both geminal R groups are polyorganosiloxanes. These types of polyorganosiloxane compounds are referred to as T-resin or Q-resin, branched or grafted, co-polymer of polyorganosiloxane polyurethane.

The polyorganosiloxane polyurethane polymers may also be prepared from functionalized isocyanate prepolymers. For example, an isocyanate prepolymer may be a di-functional or multi-functional polyorganosiloxane isocyanate, such as the polyorganosiloxane diisocynate shown below in Formula IV:

IV

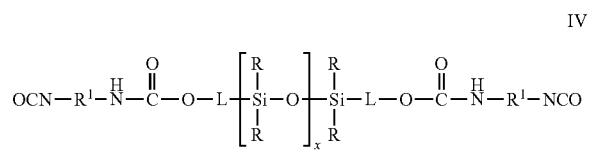

where R, $R^1$, and L as defined previously and where x is an integer from 0 to 5,000, preferably from 1 to 200, more preferably from 10 to 100, and more preferred still from 10 to 50. The prepolymer may be multi-functional as well by introducing additional isocyanate-bearing groups at one or more R groups. The isocyanate-functionalized polyorganosiloxane prepolymer is reacted with a hydroxyl-functionalized polyorganosiloxane prepolymer such as that according to Formula I or a multi-functional analog thereof. The prepolymer according to Formula IV will typically have a molecular weight ranging from about 4,000 to about 15,000 Daltons. The prepolymer according to Formulas I, Ia, and Ib will typically have a molecular weight ranging from about 250 to about 15,000 Daltons.

In a currently preferred embodiment, the polyorganosiloxane polyurethane polymer for use in the hair care compositions of the invention is co-polymer comprising the reaction product of Formula Ib with a saturated methylene diphenyl diisocyanate (SMDI). An exemplary silicone polyurethane polymer is Bis-Hydroxypropyl Dimethicone/SMDI copolymer (INCI).

A second component according to some embodiments of the inventive compositions is a high molecular weight hydrophobic ester, which can form a water-resistant hydrophobic film on the hair. The hydrophobic ester may be saturated or unsaturated and may include without limitation, mono-esters of fatty acids, diesters of diacids, diesters of triacids, and triesters of triacids. Monoesters include the esterification products of straight chained, branched, or cyclic $C_4$-$C_{24}$, preferably $C_8$-$C_{24}$, and more preferably $C_{12}$-$C_{22}$ monocarboxylic acids with straight chained, branched, or cyclic $C_4$-$C_{36}$, preferably $C_8$-$C_{24}$, and more preferably $C_{12}$-$C_{18}$ alcohols. Diesters include the esterification products of straight chained, branched, or cyclic $C_4$-$C_{48}$ dicarboxylic acids, typically $C_8$-$C_{44}$ dicarboxylic acids, and more typically $C_{12}$-$C_{36}$ dicarboxylic acids, with straight chained, branched, or cyclic $C_4$-$C_{36}$, preferably $C_8$-$C_{24}$, and more preferably $C_{12}$-$C_{28}$ alcohols. The dicarboxylic acid may be, for example, a dimer acid formed by the dimerization of an unsaturated fatty alcohol, e.g., linoleic acid. Diesters and triesters of triacids include the esterification products of $C_6$-$C_{72}$ tricarboxylic acids, typically $C_{12}$-$C_{66}$ tricarboxylic acids, with $C_4$-$C_{36}$, preferably $C_8$-$C_{24}$, and more preferably $C_{12}$-$C_{18}$ alcohols. The tricarboxylic acid may be, for example, a trimer acid formed by the trimerization of an unsaturated fatty alcohol, e.g., linoleic acid.

The esters are preferably high molecular weight esters by which is meant that the molecular weight is at least 500. In some embodiments, the molecular weight of the ester will be at least 750, at least 1000, or at least 1200. The esters are preferably hydrophobic. In the preferred practice of the invention, the ester will dispersible but not soluble in the vehicle.

One suitable hydrophobic ester is Triisostearyl Trilinoleate (INCI) (CAS Registry No. 103213-22-5), which is available from Lubrizol Advanced Materials, Inc. under the trade name SCHERCEMOL™ TIST Ester.

A third component according to some embodiments of the inventive compositions is a fluorosilicone, which can impart excellent spreading properties. The fluorosilicone is preferably hydrophobic and oleophobic and is also preferably insoluble but dispersible in the vehicle. There is essentially no restriction on the nature of the fluorosilicone. In one embodiment, the fluorosilicone will comprise a fluoro-substituted polyorganosiloxane. The fluorosilicone will typically comprise repeat units of the form —[Si($R_2$)($R_3$)—O]— wherein $R_2$ and/or $R_3$ are independently alkyl, aryl, or alkylaryl (e.g., benzyl) radicals, with at least one of $R_2$ and $R_3$ being substituted with one or more fluorine atoms. Preferably, at least one of $R_2$ or $R_3$ will be a $C_{1-30}$ alkyl group which comprises one or more fluorine atoms, and which preferably comprises a perfluoro segment, by which is meant a segment of the form —$(CF_2)_x$— where x is an integer from 1 to 29 and/or a trifluoromethyl group A preferred fluorosilicone has the following general structure of Formula V:

V

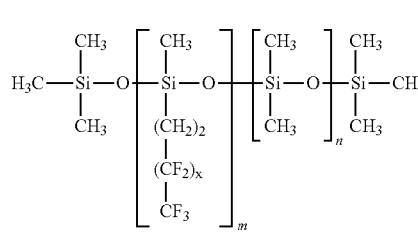

where m is an integer from 1 to 5,000, preferably from 1 to 200, more preferably from 10 to 100, and more preferred still from 10 to 50; where n is an integer from 0 to 4,999, preferably from 1 to 200, more preferably from 10 to 100, and more preferred still from 10 to 50; and wherein x is an integer from 0 to 12. One suitable fluorosilicone is Perfluorononyl Dimethicone sold under the trade names PECOSIL® FSL-150, FSL-300, FSH-150, FSH-300, FSU-150 and FSU-300 from Phoenix Chemical, Inc. which all have the chemical abstracts number CAS 259725-95-6.

The inventive hair care compositions will comprise a cosmetically acceptable vehicle. By "cosmetically acceptable" is meant that the vehicle is safe for contact with a human integument. It is contemplated that any cosmetically acceptable vehicle known in the art will be useful. The vehicle may comprise water or hydrophobic or hydrophilic organic solvents. Suitable hydrophilic solvents include but are not limited to, alcohols (e.g., ethanol, isopropanol, benzyl alcohol, phenylethyl alcohol, etc.), propylene glycol, butylene glycol, pentylene glycol, hexylene glycol, caprylyl glycol, glycerin, carbitol, glycol ethers such as, for example, ethylene glycol monomethyl, monoethyl and monobutyl ethers, ethers of propylene glycol such as, for example, propylene glycol monomethyl ether, dipropylene glycol and diethylene glycol alkyl ethers such as, for example, diethylene glycol monoethyl ether or monobutyl ether, and or any combinations thereof. Water is a preferred vehicle component. Typically, the amount of water in the vehicle is about 20% to about 99%, more typically from about 60% to about 95% by weight.

Suitable hydrophobic vehicles include hydrocarbon oils, which may be saturated or unsaturated, have an aliphatic character and be straight or branched chained or contain alicyclic or aromatic rings. Essentially any oil is contemplated to be useful, although highly hydrophobic oils are preferred. Suitable non-limiting examples include vegetable oils; esters such as octyl palmitate, isopropyl myristate and isopropyl palmitate; ethers such as dicapryl ether; fatty alcohols such as cetyl alcohol, stearyl alcohol and behenyl alcohol, isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; natural or synthetic waxes; and the like.

Suitable hydrophobic hydrocarbon oils may be saturated or unsaturated, have an aliphatic character and be straight or branched chained or contain alicyclic or aromatic rings. Hydrocarbon oils include those having 6-20 carbon atoms, more preferably 10-16 carbon atoms. Representative hydrocarbons include decane, dodecane, tetradecane, tridecane, and $C_{8-20}$ isoparaffins. Paraffinic hydrocarbons are available from Exxon under the ISOPARS trademark, and from the Permethyl Corporation. In addition, $C_{8-20}$ paraffinic hydrocarbons such as $C_{12}$ isoparaffin (isododecane) manufactured by the Permethyl Corporation having the tradename Permethyl 99A™ are also contemplated to be suitable. Various commercially available $C_{16}$ isoparaffins, such as isohexadecane (having the tradename Permethyl R™) are also suitable. Examples of preferred volatile hydrocarbons include polydecanes such as isododecane and isodecane, including for example, Permethyl-99A (Presperse Inc.) and the $C_7$-$C_8$ through $C_{12}$-$C_{15}$ isoparaffins such as the Isopar Series available from Exxon Chemicals. A representative hydrocarbon solvent is isododecane.

The vehicle may comprise a silicone oil phase which may include volatile silicone oils, non-volatile silicone oils, and combinations thereof. By volatile silicone oil is meant that the oil readily evaporates at ambient temperatures. Typically, volatile silicone oils will exhibit a vapor pressure ranging from about 1 Pa to about 2 kPa at 25° C.; will preferably have a viscosity of from about 0.1 to about 10 centistokes, preferably about 5 centistokes or less, more preferably about 2 centistokes or less, at 25° C.; and will boil at atmospheric pressure at from about 35° C. to about 250° C.

Volatile silicones include cyclic and linear volatile dimethylsiloxane silicones. In one embodiment, the volatile silicones may include cyclodimethicones, including tetramer (D4), pentamer (D5), and hexamer (D6) cyclomethicones, or mixtures thereof. Particular mention may be made of the volatile cyclomethicone-hexamethyl cyclotrisiloxane, octamethyl-cyclotetrasiloxane, and decamethyl-cyclopentasiloxane. Suitable dimethicones polymers are available from Dow Corning under the name Dow Corning 200® Fluid and have viscosities ranging from 0.65 to 600,000 centistokes or higher. Suitable non-polar, volatile liquid silicone oils are disclosed in U.S. Pat. No. 4,781,917, herein incorporated by reference in its entirety. Additional volatile silicones materials are described in Todd et al., "Volatile Silicone Fluids for Cosmetics", Cosmetics and Toiletries, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of volatile silicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones), GE 7207 and 7158 (General Electric Co.); and SWS-03314 (SWS Silicones Corp.). Linear, volatile silicones include low molecular weight polydimethylsiloxane compounds such as hexamethyldisiloxane, octamethyltrisiloxane, decamethyltetrasiloxane, and dodecamethylpentasiloxane to name a few.

Non-volatile silicone oils will typically comprise polyalkylsiloxanes, polyarylsiloxanes, polyalkylarylsiloxanes, or mixtures thereof. Polydimethylsiloxanes are preferred non-volatile silicone oils. The non-volatile silicone oils will typically have a viscosity from about 10 to about 60,000 centistokes at 25° C., preferably between about 10 and about 10,000 centistokes, and more preferred still between about 10 and about 500 centistokes; and a boiling point greater than 250° C. at atmospheric pressure. Non limiting examples include dimethyl polysiloxane (dimethicone), phenyl trimethicone, and diphenyldimethicone.

The vehicle may comprise a single phase, a dual-phase system, or an emulsion. Emulsions include oil-in-water, silicone-in-water, water-in-oil, water-in-silicone, and the like. When formulated as an emulsion, an emulsifier is typically included. Where the product is intended as a spray, it may be desirable to employ a single phase vehicle, or a dual phase vehicle comprising an aqueous phase and an oil phase, the oil phase comprising a silicone oil. Alternatively, it is contemplated that the vehicle may be anhydrous. The anhydrous vehicle preferably comprises a silicone oil. It is to be understood that the term "anhydrous" as used herein typically refers to a composition comprising at most 5% water, more typically to a composition comprising at most 1% water, and usually a composition comprising an amount of water absorbed from ambient conditions.

In one embodiment, the inventive combination of a silicone polyurethane polymer, film-forming ester, and fluorosilicone is dispersible but not soluble in the vehicle. It has unexpectedly been found that the fading of hair color is markedly retarded when the combination is formulated in an incompatible vehicle when compared to an otherwise identical vehicle in which the combination is more compatible. Without wishing to be bound by any theory, it is believed that the phase separation provides improved deposition of the inventive combination onto keratin fibers of the hair and thereby improving the coverage of water-resistant films formed therefrom that serve as protective barriers against water and/or shampoo.

In a preferred embodiment, the vehicle is a thickened aqueous system comprising water and a thickener. The thickener may be nonionic, cationic, anionic or amphoteric. Preferably, the thickener is a cationic thickener, including without limitation cationic conditioning polymers. Suitable cationic polymers include, but are not limited to, cationized cellulose, cationized guar gum, diallyly quaternary ammonium salt/acrylamide copolymers, polyquaternium-37, and mixtures thereof. Among the various cationic thickeners, special mention may be made of polyquaternium-37 (INCI).

Other suitable thickeners can include, for example, acrylic acid homopolymers (sold under the trade name CARBOPOL® by Lubrizol Corp.), acrylates/$C_{10-30}$ alkyl acrylate crosspolymer (available under the trade names CARBOPOL® 1342 and 1382; and PEMULINS® TR-1 and TR-2 from BF Goodrich), Acrylates/Steareth-20 Itaconate copolymer (available under the trade name STRUCTURE® 2001 from National Starch), Acrylates/Ceteth-20 Itaconate copolymer (available under the trade name STRUCTURE® 3001 from National Starch), bentonite, PVM/MA Decadiene Crosspolymer, which is a crosspolymer of methylvinylether/maleic anhydride copolymer cross-linked with 1, 9 decadiene (commercially available under the trade name STABILEZE® QM from International Specialties Products), Acrylates/steareth-20 methacrylate copolymer (sold under the trade name ACRYSOL™ ICS-1 by Rohm and Haas Co.), acrylamide/sodium acrylate copolymer (sold under the trade name HOSTACERIN® PN 73 by Hoecsht AG), acrylate copolymer (sold under the trade name ANTIL 208 by Goldschmidt), acrylic acid/acrylonitrogens copolymer (sold under the trade names HYPAN® SA-100H, SR-150H supplied by Lipo), Acrylic/acrylate copolymer (sold under the trade names CARBOSET® 5 514, 515, 525, XL-19, XL-19X2, X1-28, XL-40, 526 by BF Goodrich), Ammonium acrylates/acrylonitrogens copolymer (sold under the trade name HYPAN® SS-201 by Lipo), Quaternium-18 Bentonite, which is a sodium salt of crosslinked poly(acrylic acid) (sold under the tradenames PNC 430, PNC 410, PNC 400 by 3V), Stearalkonium Bentonite (sold under the trade name CLAYTON® by Southern Clay Products), Quaternium-18 Hectorite (Bentone 38), Stearalkonium Hectorite (Bentone 27), Poly(acrylic acid) (sold under the trade names CARBOPOL® 400 by BF and AQUATREAT® by Alco), trihydroxystearin (commercially available under the trade names THIXICIN® by Rheox and FLOWTONE™ by Southern Clay Products), Dimethylaminoethyl methacrylamide and acrylamide copolymer (SALCARE® SC63 from Ciba Specialties), Acrylic polymer anionic or cationic thickening agents (sold under the trade name SYNTHALEN™ by 3V), Polyacrylate-1 crosspolymer (INCI) (sold under the trade name CARBOPOL® Aqua CC by Lubrizol Corp.), Sodium Acrylate copolymer (sold under the trade name TINOVIS® ADM by Ciba), and Polyacrylamidomethylpropane Sulfonic Acid (sold under the trade name Cosmedia HSP-1180 by Cognis Care Chemicals).

The thickener preferably comprises from about 0.001 to about 25%, more preferably at about 0.1% to about 15%, and more preferred still from about 0.5% to about 5% by weight of the vehicle.

The silicone polyurethane polymer, film-forming ester, and fluorosilicone will collectively comprise from about 1% to about 50% by weight of the total composition including the vehicle. More typically, silicone polyurethane polymer, film-forming ester, and fluorosilicone will collectively comprise from about 1% to about 25% by weight, or from about 1% to about 10% by weight of the total composition including the vehicle.

The compositions of the invention may optionally comprise other active and inactive ingredients typically associated with hair care products. The nature of these other ingredients and their amounts should preferably be suitable for formulating a stable hair care product which forms a hydrophobic film on keratin fibers. Preferably, these other ingredients include at least one bioactive ingredient for improving the keratin fiber. It is within the skill in the art to choose additional active and/or inactive ingredients for a hair care product. Suitable other ingredients include, but are not limited to, amino acids, antioxidants, chelating agents, colorants, emollients, emulsifiers, excipients, fillers, fragrances, gelling agents, humectants, minerals, moisturizers, photostabilizing agents (e.g., UV absorbers), preservatives, stabilizers, staining agents, surfactants, viscosity and/or rheology modifiers, vitamins, waxes and mixtures thereof. It is contemplated that the inventive hair care product of the present invention can also include anti-dandruff, deodorant, sunscreen and/or antiperspirant ingredients.

The compositions may be in any suitable form, including but not limited to gels, creams, liquids, emulsions, sprays, and the like.

The present invention provides a method for improving color retention and/or reducing color fading of artificially colored hair comprising applying to a keratin fiber a hair care composition having a combination of a silicone polyurethane polymer, a film-forming ester, and a fluorosilicone in a suitable vehicle. However, the invention is not limited to application to artificially colored hair. The methods and composition may be applied to any hair (whether dyed or not) to impart a water-resistant film on the keratin fiber.

The hair care composition of the present invention may be applied to wet or dry hair at any time after artificially coloring the hair using chemical dyes. Preferably, the hair care composition is applied to the hair after it has been artificially colored, but before the first wash. More preferably, the hair care composition is applied to the hair immediately following artificially coloring the hair with chemical dyes. However, significant benefits will be obtained even if the composition is applied to the hair after the first shampooing, or even after the second or third shampooing. In addition, the hair care composition can be re-applied at any time, as the consumer desires. In one embodiment, the hair care composition may be re-applied to the hair before every wash.

While the currently preferred embodiments of the inventive formulations comprise all three components (silicone polyurethane, ester, and fluorosilicone), the invention is not so limited. In some embodiments the inventive compositions will comprise two of these three components. Thus, the following combinations are considered to be within the scope of the invention: silicone polyurethane and hydrophobic ester; silicone polyurethane and fluorosilicone; and hydrophobic ester and fluorosilicone. These compositions may comprise the two components in weight ratios from about 10:1 to about 1:10, or from about 5:1 to about 1:5, or from about 2:1 to about 1:2, or about 1:1. In some embodiments, it is believed that the two-component combinations will impart at least an additive improvement in color-retention, and preferably a synergistic improvement.

EXAMPLE I

Compositions comprising a silicone polyurethane polymer, high molecular weight ester, and fluorosilicone in a 1:1:1 weight ratio were prepared according to Table 1 wherein the vehicle was either (i) and oil-in-water emulsion system, or (ii) and aqueous system comprising water thickened with polyquaternium-37.

TABLE 1

| Component | Weight % |
|---|---|
| Bis Hydroxypropyl Dimethicone/Saturated | 2% |

TABLE 1-continued

| Component | Weight % |
|---|---|
| Methylene Diphenyl Diisocyanate (SMDI) copolymer | |
| SCHERCEMOL ™ TIST Ester - Triisostearyl Trilinoleate (Lubrizol Advanced Materials, Inc.) | 2% |
| PECOSIL ® Perfluorononyl Dimethicone (Phoenix Chemical, Inc.) | 2% |
| vehicles (i) or (ii) | q.s. |
| Total | 100% |

The color retention of artificially colored hair treated with the hair care compositions comprising each vehicle. Hair samples were treated with a chemical dye having red tones, to impart an artificial hair color and then treated with the inventive composition. The hair samples were then washed with a commercial shampoo product sold under the designation ADVANCED TECHNIQUES™ (Avon Products, Inc.) and rinsed with water. The treatment, washing and rinsing cycles were repeated fifteen (15) times. Color retention was noticeably better for the hair samples treated with the composition in the cationic-thickened aqueous base as compared to the oil-in-water emulsion.

EXAMPLE II

The effect of adding Triisostearyl Trilinoleate (INCI), a high molecular weight hydrophobic ester, in combination with a silicone polyurethane and/or a fluorosilicone to a hair care composition was investigated in relation to the color retention of dyed hair treated with the hair care composition. Compositions were prepared according to Table 2 wherein the vehicle was either (i) a conventional hair conditioner composition (Vehicle A); (ii) an aqueous system comprising water thickened with a cationic compound (Vehicle B), or (iii) a biphasic system comprising water and a silicone oil (Vehicle C).

TABLE 2

| Components | Vehicle | Sample Number: | | | | | | | | | |
|---|---|---|---|---|---|---|---|---|---|---|---|
| | | 1 | 2 | 3 | 4 | 5 | 6 | 7 | 8 | 9 | 10 |
| | | | | | | Weight % | | | | | |
| SCHERCEMOL ™ TIST Ester--Triisostearyl Trilinoleate (Lubizol Advanced Materials, Inc.). | — | 2 | — | — | 5 | — | — | 1 | 1 | 2 | 2 |
| Bis-Hydroxypropyl Dimethicone/ SMDI copolymer | — | — | 2 | — | — | 5 | — | 2 | — | — | 2 |
| PECOSIL ® Perfluorononyl Dimethicone (Phoenix Chemical, Inc.) | — | — | — | 2 | — | — | 5 | — | 2 | 2 | 2 |
| Vehicle (A, B or C) | 100 | q.s. | q.s. | q.s. | q.s. | q.s. | q.s. | q.s. | q.s. | q.s. | q.s. |
| Total | 100 | 100 | 100 | 100 | 100 | 100 | 100 | 100 | 100 | 100 | 100 |

The vehicles for the hair care compositions were prepared according to Table 3 below.

TABLE 3

| Components | Vehicle: | | |
|---|---|---|---|
| | A | B | C |
| | Weight % | | |
| Citric Acid | 0.03 | — | — |
| Cetrimonium Chloride (50% solution in water) | 2.0 | — | — |
| Cetyl/Stearyl Alcohol | 4.0 | — | — |
| Preservatives | 0.8 | — | 0.7 |
| Perfume | 0.4 | — | — |
| SALCARE ® SC-96 Polyquaternium-37 (Ciba) | — | 2.0 | — |
| Cyclomethicone | — | — | 45 |
| Water | q.s. | q.s. | q.s. |
| Total | 100 | 100 | 100 |

The color retention of artificially colored hair treated with the hair care compositions comprising each vehicle were examined using the testing protocol described below.

Color Retention Test Method

Hair samples were treated with a commercial chemical dye CLAIROL HYDRIENCE™, Ruby Twilight 3RR (Procter & Gamble) or L'OREAL PREFERENCE Medium Brown (L'Oreal) according to the manufacturers' instructions. Each hair sample was rinsed under running warm water for 5 minutes. Each hair sample was dabbed dry with a towel to remove most of the retained moisture. Using a pipette, 0.5 mL of a hair care composition was placed on to the hair sample and manually distributed throughout by repeat downward motions. The hair sample was left to air dry at room temperature for 72 hours. Each hair sample was then washed, rinsed, treated and dried a total of fifteen (15) times.

Each time, the hair sample is first rinsed under running warm water, at a temperature between 100 to 110° F., for 30 seconds. Excess water from the hair samples were manually removed by squeezing the hair samples between the middle and index fingers.

To wash each hair sample, 0.5 mL of a commercial shampoo is applied to the hair sample using a pipette. The shampoo is manually distributed throughout the hair sample by applying repeat downward motions for 30 seconds. The shampooed hair sample is placed under running warm water, at a temperature between 100 to 110° F., and rinsed for 30 seconds. Excess water from the hair sample was manually removed by squeezing the hair sample between the middle and index fingers. Using a pipette, 0.5 mL of a hair care composition was placed on to the hair sample and manually distributed throughout by repeat downward motions.

The hair sample treated with the hair care composition was left to air dry in an oven at an elevated temperature of 120° F. until all of the residual moisture in the hair sample has been evaporated. Once the hair sample has been dried, the hair sample is repeatedly subject to the rinsing, washing, rinsing, treating and drying steps an additional fourteen (14) times.

The color retention of each hair sample is visually assessed by comparison to a control hair sample, which is a hair sample artificially colored with the same commercial chemical dye according to manufacturer's instruction, untreated with any other hair care compositions, and not subject to repeat washing and drying. The results are shown below in Table 4. Hair samples treated with hair care compositions that clearly provide color retention of dyed hair are represented in Table 4 with two asterisks ("**"), whereas hair samples treated with hair care compositions that provide some color retention are represented with one asterisk ("*").

TABLE 4

|  | Vehicle A | Vehicle B | Vehicle C |
|---|---|---|---|
| Shampoo only |  |  |  |
| Vehicle |  | * |  |
| Sample 1 |  |  |  |
| Sample 2 |  |  |  |
| Sample 3 |  |  |  |
| Sample 4 |  |  | ** |
| Sample 5 | ** | ** | ** |
| Sample 6 |  | ** | ** |
| Sample 7 | ** |  | * |
| Sample 8 |  | ** | * |
| Sample 9 | ** | ** |  |
| Sample 10 | ** | ** |  |

The results indicate that Triisostearyl Trilinoleate in combination with a fluorosilicone, specifically Perfluorononyl Dimethicone, in a conventional hair conditioner composition act synergistically to improve the color retention of dyed hair treated with said hair conditioner composition. As shown in Table 4, the combination of 2% by weight of Triisostearyl Trilinoleate and Perfluorononyl Dimethicone (e.g., Sample 9) in Vehicle A provides superior color retention than the addition of Triisostearyl Trilinoleate, in the absence of a fluorosilicone, and the addition of Perfluorononyl Dimethicone, in the absence of a high molecular weight hydrophobic ester. As can be seen from the results in Table 4, the addition of up to 5% by weight of Triisostearyl Trilinoleate to Vehicle A, in the absence of a fluorosilicone (Samples 1 and 4) does not provide any visible improvements to the retention of artificial hair color. Similarly, the addition of up to 5% by weight of Perfluorononyl Dimethicone to Vehicle A, in the absence of a high molecular weight hydrophobic ester (Samples 3 and 6) also does not provide any visible improvements to the retention of artificial hair color.

A lower threshold amount of Triisostearyl Trilinoleate may be needed when the combination of Triisostearyl Trilinoleate and a fluorosilicone is used with an aqueous system comprising water thickened with a cationic compound. The results show that the addition of as low as 1% by weight of Triisostearyl Trilinoleate in combination with Perfluorononyl Dimethicone (Samples 8 and 9) in an aqueous system comprising water thickened with a cationic compound (Vehicle B) provided visible improvements in the color retention of artificial hair colors. In contrast, the addition of up to 5% by weight of Triisostearyl Trilinoleate to Vehicle B, in the absence of a fluorosilicone (Samples 1 and 4) does not provide any visible improvements to the retention of artificial hair color. The addition of Perfluorononyl Dimethicone to Vehicle B, in the absence of a high molecular weight hydrophobic ester, provided visible improvements to color retention only when the amount of Perfluorononyl Dimethicone was increased to 5%. Therefore, the results show that in Vehicle B, the combination of Triisostearyl Trilinoleate and a fluorosilicone is at least additive, if not synergistic, and that there is a low threshold amount of Triisostearyl Trilinoleate needed for there to be a visible color retention effect.

The invention claimed is:

1. A method for improving color retention of artificially colored hair comprising applying to hair that has been dyed with an oxidative dye, after it has been dyed but prior to a first shampooing, a composition comprising (i) a silicone polyurethane polymer, comprising Bis-hydroxypropyl Dimethicone/dicyclohexylmethane-4,4'-diisocyanate (SMDI) copolymer (INCI)

(ii) a film-forming ester comprising a tri-ester of a $C_6$-$C_{72}$ tricarboxylic acid with a branched $C_8$-$C_{24}$ alcohol;

(iii) fluorosilicone, and (iv) a vehicle;

wherein said silicone polyurethane polymer, said film-forming ester, and said fluorosilicone are dispersible but not soluble in said vehicle.

2. The method according to claim 1, wherein said composition comprises from 1 to 5 parts of said silicone polyurethane polymer, from 1 to 5 parts of said film-forming ester, and from 1 to 5 parts of said fluorosilicone, on a weight basis.

3. The method according to claim 1, wherein the weight ratio of silicone polyurethane polymer to film-forming ester to fluorosilicone is about 1:1:1.

4. The method according to claim 1, wherein the molecular weight of said film-forming ester is greater than about 1000.

5. The method according to claim 4, wherein said film-forming ester is Triisostearyl Trilinoleate (INCI).

6. The method according to claim 1, wherein said fluorosilicone has the structure:

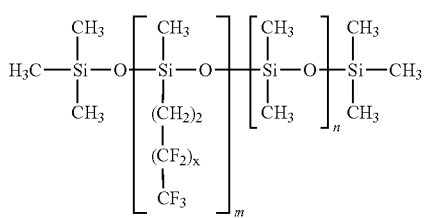

where m is an integer from 1 to 5,000,
where n is an integer from 0 to 4,999, and
where x is an integer from 0-to 12.

7. The method according to claim 1, wherein the fluorosilicone comprises Perfluorononyl Dimethicone (INCI).

8. The method according to claim 1, wherein the vehicle comprises water and a thickener.

9. The method according to claim 8, wherein said thickener is a cationic thickener.

10. The method according to claim 9, wherein said cationic thickener is Polyquaternium-37 (INCI).

11. The method according to claim 1, wherein said silicone polyurethane polymer, said film-forming ester, and said fluorosilicone, collectively comprise from about 1% to about 20% by weight of the composition.

12. The method according to claim 1, wherein said silicone polyurethane polymer, said film-forming ester, and said fluorosilicone, collectively comprise from about 1% to about 10% by weight of the composition.

13. The method according to claim 1, wherein said composition is re-applied to the hair after the first shampooing but prior to a second shampooing.

14. A method for improving color retention of artificially colored hair comprising applying to hair that has been dyed with an oxidative dye, after it has been dyed, a composition comprising:
(i) Bis-Hydroxypropyl Dimethicone/SMDI copolymer;
(ii) Triisotearyl Trilinoleate;
(iii) Perfluorononyl Dimethicone; and
(iv) a vehicle;
wherein at least one of said Bis-Hydroxypropyl Dimethicone/SMDI copolymer, said Triisotearyl Trilinoleate, and said Perfluorononyl Dimethicone are dispersible but not soluble in said vehicle.

15. The method according to claim 14, wherein each of said Bis-Hydroxypropyl Dimethicone/SMDI copolymer, Triisotearyl Trilinoleate, and Perfluorononyl Dimethicone are dispersible but not soluble in said vehicle.

16. The method according to claim 14 wherein said vehicle comprises water and a cationic thickener.

\* \* \* \* \*